(12) United States Patent
Gilbert et al.

(10) Patent No.: US 9,011,797 B2
(45) Date of Patent: Apr. 21, 2015

(54) MICROFLUIDIC SYSTEM INCLUDING A BUBBLE VALVE FOR REGULATING FLUID FLOW THROUGH A MICROCHANNEL

(75) Inventors: John R. Gilbert, Brookline, MA (US); Sebastian Böhm, Iverness (GB); Manish Deshpande, Canton, MA (US)

(73) Assignee: Cytonome/ST, LLC, Boston, MA (US)

( * ) Notice: Subject to any disclaimer, the term of this patent is extended or adjusted under 35 U.S.C. 154(b) by 0 days.

(21) Appl. No.: 13/527,331

(22) Filed: Jun. 19, 2012

(65) Prior Publication Data
US 2012/0261013 A1 Oct. 18, 2012

Related U.S. Application Data

(63) Continuation of application No. 11/433,781, filed on May 12, 2006, now Pat. No. 8,210,209, which is a continuation of application No. 11/021,251, filed on Dec. 21, 2004, now Pat. No. 7,069,943, which is a continuation of application No. 10/179,586, filed on Jun. 24, 2002, now Pat. No. 6,877,528.

(60) Provisional application No. 60/373,256, filed on Apr. 17, 2002.

(51) Int. Cl.
*B81B 3/00* (2006.01)
*B01L 3/00* (2006.01)
(Continued)

(52) U.S. Cl.
CPC ..... *B01L 3/502738* (2013.01); *B01L 3/502761* (2013.01); *B01L 3/502776* (2013.01); *B01L 2200/0636* (2013.01); *B01L 2200/0647* (2013.01); *B01L 2300/0816* (2013.01); *B01L 2300/0864* (2013.01); *B01L 2300/089* (2013.01); *B01L 2400/0415* (2013.01); *B01L 2400/06* (2013.01); *B01L 2400/0688* (2013.01); *B01L 2400/082* (2013.01); *B07C 5/34* (2013.01); *F16K 99/0001* (2013.01); *F16K 99/0017* (2013.01); *F16K 99/0019* (2013.01);
(Continued)

(58) Field of Classification Search
CPC ............... B01L 2200/0636; B01L 2300/0864; B01L 2400/082; B01L 3/502761; G01N 2015/149
USPC .................. 422/502–505; 251/61.1; 436/177
See application file for complete search history.

(56) References Cited

U.S. PATENT DOCUMENTS 3,289,687 A 12/1966 Dunaway
3,370,538 A 2/1968 Iliacs
(Continued)

FOREIGN PATENT DOCUMENTS

EP A 0 177 718 4/1986
EP A 0 745 682 12/1996
(Continued)

OTHER PUBLICATIONS

International Search Report issued in International Application No. PCT/US2003/12368, dated Aug. 21, 2003.
(Continued)

*Primary Examiner* — Paul Hyun
(74) *Attorney, Agent, or Firm* — McCarter & English, LLP; David R. Burns

(57) ABSTRACT

A microfluidic system includes a bubble valve for regulating fluid flow through a microchannel. The bubble valve includes a fluid meniscus interfacing the microchannel interior and an actuator for deflecting the membrane into the microchannel interior to regulate fluid flow. The actuator generates a gas bubble in a liquid in the microchannel when a sufficient pressure is generated on the membrane.

19 Claims, 8 Drawing Sheets

(51) Int. Cl.
  *B07C 5/34* (2006.01)
  *F16K 99/00* (2006.01)
  *G01N 15/14* (2006.01)

(52) U.S. Cl.
  CPC ......... *F16K99/0034* (2013.01); *F16K 99/0036* (2013.01); *F16K 99/004* (2013.01); *F16K 99/0046* (2013.01); *F16K 99/0048* (2013.01); *F16K 2099/0074* (2013.01); *F16K 2099/008* (2013.01); *F16K 2099/0084* (2013.01); *G01N 2015/149* (2013.01)

(56) References Cited

U.S. PATENT DOCUMENTS

| | | | |
|---|---|---|---|
| 3,508,654 | A | 4/1970 | Glaettli |
| 3,560,754 | A | 2/1971 | Kamentsky |
| 3,791,517 | A | 2/1974 | Friedman |
| 3,827,555 | A | 8/1974 | Kamnetsky |
| 3,984,307 | A | 10/1976 | Kamnetsky |
| 4,153,855 | A | 5/1979 | Feingold |
| 4,175,662 | A | 11/1979 | Zold |
| 4,426,451 | A | 1/1984 | Columbus |
| 4,581,624 | A | 4/1986 | O'Connor |
| 4,636,149 | A | 1/1987 | Brown |
| 4,676,274 | A | 6/1987 | Brown |
| 4,756,427 | A | 7/1988 | Gohde et al. |
| 4,908,112 | A | 3/1990 | Pace |
| 5,065,978 | A | 11/1991 | Albarda et al. |
| 5,092,972 | A | 3/1992 | Ghowsi |
| 5,101,978 | A | 4/1992 | Marcus |
| 5,265,327 | A | 11/1993 | Faris et al. |
| 5,777,649 | A | 7/1998 | Otsuka et al. |
| 5,789,045 | A | 8/1998 | Wapner et al. |
| 5,837,200 | A | 11/1998 | Diessel et al. |
| 5,876,187 | A | 3/1999 | Afromowitz et al. |
| 5,988,522 | A | 11/1999 | Glezer et al. |
| 6,033,191 | A | 3/2000 | Kamper et al. |
| 6,048,328 | A | 4/2000 | Haller et al. |
| 6,048,734 | A | 4/2000 | Burns et al. |
| 6,062,681 | A | 5/2000 | Field et al. |
| 6,102,530 | A | 8/2000 | Kim et al. |
| 6,152,181 | A | 11/2000 | Wapner et al. |
| 6,196,525 | B1 | 3/2001 | Ganan-Calvo |
| 6,203,291 | B1 | 3/2001 | Stemme et al. |
| 6,221,654 | B1 | 4/2001 | Quake et al. |
| 6,273,553 | B1 | 8/2001 | Kim et al. |
| 6,360,775 | B1 | 3/2002 | Barth et al. |
| 6,432,630 | B1 | 8/2002 | Blankenstein |
| 6,561,224 | B1 | 5/2003 | Cho |
| 6,592,821 | B1 | 7/2003 | Wada et al. |
| 6,597,438 | B1 | 7/2003 | Cabuz et al. |
| 6,629,820 | B2 | 10/2003 | Korselsen |
| 6,802,342 | B2 | 10/2004 | Fernandes et al. |
| 6,877,528 | B2 | 4/2005 | Gilbert et al. |
| 7,069,943 | B2 | 7/2006 | Gilbert et al. |
| 8,210,209 | B2 | 7/2012 | Gilbert et al. |
| 2002/0166585 | A1* | 11/2002 | O'Connor et al. ......... 137/87.01 |
| 2006/0278288 | A1 | 12/2006 | Gilbert et al. |
| 2012/0015442 | A1 | 1/2012 | Gilbert et al. |

FOREIGN PATENT DOCUMENTS

| | | |
|---|---|---|
| WO | WO 91/15750 | 10/1991 |
| WO | WO 98/07069 | 2/1998 |
| WO | WO 98/10267 | 3/1998 |
| WO | WO 00/70080 | 11/2000 |

OTHER PUBLICATIONS

International Preliminary Examination Report issued in International Application No. PCT/US2003/12368, dated Aug. 25, 2004.
International Search Report issued in International Application No. PCT/US2003/12360, dated Oct. 3, 2003.
International Preliminary Examination Report issued in International Application No. PCT/US2003/12360, dated Jul. 21, 2004.
International Search Report issued in International Application No. PCT/US2003/12359, dated Sep. 2, 2003.
International Preliminary Examination Report issued in International Application No. PCT/US2003/12359, dated Sep. 5, 2004.
Supplementary European Search Report issued in European Application No. 03726391.0-2204, dated Oct. 6, 2009.
Communication pursuant to Article 94(3) EPC issued in European Application No. 03726391.0-2204, dated Apr. 12, 2010.
Search Information Statement issued in Australian Application No. 2010200179, dated Mar. 21, 2011.
Examiner's Report issued in Australian Application No. 2010200179, dated Mar. 22, 2011.

* cited by examiner

MICROFLUIDIC SYSTEM INCLUDING A BUBBLE VALVE FOR REGULATING FLUID FLOW THROUGH A MICROCHANNEL

RELATED APPLICATIONS

This application is a continuation of U.S. patent application Ser. No. 11/433,781, entitled "Microfluidic System Including a Bubble Valve for Regulating Fluid Flow Through A Microchannel", filed on May 12, 2006, which is a continuation of U.S. patent application Ser. No. 11/021,251 filed Dec. 21, 2004 which, in turn, is a continuation of U.S. patent application Ser. No. 10/179,586 filed Jun. 24, 2002, which claims priority to U.S. Provisional Patent Application No. 60/373,256 filed Apr. 17, 2002; and is related to U.S. patent application Ser. No. 10/179,488, entitled "Method and Apparatus for Sorting Particles", filed Jun. 24, 2002. The contents of all of the above-referenced applications are herein incorporated by reference in their entirety.

FIELD OF THE INVENTION

The present invention relates to microscale fluid handling devices and systems. More particularly, the present invention relates to a method and system for controlling liquid flow in a microchannel by the introduction of a gas bubble to a microfluidic system.

BACKGROUND OF THE INVENTION

In the chemical, biomedical, bioscience and pharmaceutical industries, it has become increasingly desirable to perform large numbers of chemical operations, such as reactions, separations and subsequent detection steps, in a highly parallel fashion. The high throughput synthesis, screening and analysis of (bio)chemical compounds, enables the economic discovery of new drugs and drug candidates, and the implementation of sophisticated medical diagnostic equipment. Of key importance for the improvement of the chemical operations required in these applications are an increased speed, enhanced reproducibility, decreased consumption of expensive samples and reagents, and the reduction of waste materials.

Microfluidic devices and systems provide improved methods of performing chemical, biochemical and biological analysis and synthesis. Microfluidic devices and systems allow for the performance of multi-step, multi-species chemical operations in chip-based micro chemical analysis systems. Chip-based microfluidic systems generally comprise conventional 'microfluidic' elements, particularly capable of handling and analyzing chemical and biological specimens. Typically, the term microfluidic in the art refers to systems or devices having a network of processing nodes, chambers and reservoirs connected by channels, in which the channels have typical cross-sectional dimensions in the range between about 1.0 µm and about 500 µm. In the art, channels having these cross-sectional dimensions are referred to as 'microchannels'.

By performing the chemical operations in a microfluidic system, potentially a number of the above-mentioned desirable improvements can be realized. Downscaling dimensions allows for diffusional processes, such as heating, cooling and passive transport of species (diffusional mass-transport), to proceed faster. One example is the thermal processing of liquids, which is typically a required step in chemical synthesis and analysis. In comparison with the heating and cooling of liquids in beakers as performed in a conventional laboratory setting, the thermal processing of liquids is accelerated in a microchannel due to reduced diffusional distances. Another example of the efficiency of microfluidic systems is the mixing of dissolved species in a liquid, a process that is also diffusion limited. Downscaling the typical dimensions of the mixing chamber thereby reduces the typical distance to be overcome by diffusional mass-transport, and consequently results in a reduction of mixing times. Like thermal processing, the mixing of dissolved chemical species, such as reagents, with a sample or precursors for a synthesis step, is an operation that is required in virtually all chemical synthesis and analysis processes. Therefore, the ability to reduce the time involved in mixing provides significant advantages to most chemical synthesis and analysis processes.

Another aspect of the reduction of dimensions is the reduction of required volumes of sample, reagents, precursors and other often very expensive chemical substances. Milliliter-sized systems typically require milliliter volumes of these substances, while microliter sized microfluidic systems only require microliters volumes. The ability to perform these processes using smaller volumes results in significant cost savings, allowing the economic operation of chemical synthesis and analysis operations. As a consequence of the reduced volume requirement, the amount of chemical waste produced during the chemical operations is correspondingly reduced.

In microfluidic systems, regulation of minute fluid flows through a microchannel is of prime importance, as the processes performed in these systems highly depend on the delivery and movement of various liquids such as sample and reagents. A flow control device may be used to regulate the flow of liquid through a microchannel. Regulation includes control of flow rate, impeding of flow, switching of flows between various input channels and output channels as well as volumetric dosing.

U.S. Pat. No. 6,062,681 describes a bubble valve for a liquid flow channel in which the flow of a liquid is controlled by the generation of a gas bubble in the channel using a heater placed in the liquid. As the heater is activated, a bubble is formed which can be enlarged or reduced in size by increasing or decreasing, respectively, the temperature of the heater. The described system presents a number of disadvantages, namely, the required power to operate the valve and the inherent requirement that liquid in the channel be heated upon passing the valve. Even small increases in liquid temperature, by only a couple of degrees, can have disastrous effects on the highly heat sensitive biochemical substances present in the liquids to be controlled in many microfluidic systems. In addition, the required on-chip electric circuitry for the heater increases the complexity of the described valve and consequently results in unacceptably high costs, particularly if the fluidic system employing the bubble valve only used for a single application.

Other valves in the prior art use electrochemical means to produce a bubble in a liquid.

SUMMARY OF THE INVENTION

The present invention provides a bubble valve for controlling, regulating or varying fluid flow through a microfluidic system. The bubble valve regulates fluid flow through a channel using an, externally operated mechanical or pneumatic actuator. The actuator causes a deflection of a fluid meniscus into the interior of the channel to regulate liquid flow. The actuator may mechanically force a gas bubble into a fluid carrying microchannel to inhibit liquid flow or to cause liquid flow by applying a sufficiently high pressure to the meniscus.

The bubble valve effectively controls the flow of liquids in microfluidic systems, without heating the fluid and without complex on-chip circuitry.

The microfluidic system includes a microchannel and a sealed, gas-filled reservoir positioned adjacent to and connected to the microchannel. The gas filled reservoir has a movable wall and a meniscus formed by a liquid in the microchannel that forms an interface between the reservoir and the microchannel interior. The meniscus may form a portion of the side wall of the microchannel. An external mechanical actuator may be used to deflect the movable wall of the reservoir. As the movable wall is deflected, the volume of the reservoir decreases and the gas pressure inside the reservoir increases, causing the meniscus to deflect into the microchannel, thereby modifying the cross-sectional area of the microchannel and consequently varying the flow of liquid through the channel. The increased pressure in the reservoir pushes gas from the reservoir into the microchannel. The gas may result in a local gas bubble being forced into the microchannel from the gas-filled reservoir. The resulting gas bubble occupies a portion of the cross-section of the channel, allowing liquid flow through the channel to be effectively controlled by controlling the size of the gas bubble via the external actuator.

The meniscus may comprise a virtual wall formed in a side wall of the microchannel. The virtual wall is a meniscus formed by a liquid in the microchannel that fills an aperture formed in the side wall of the microchannel and essentially replaces the removed portion of the side wall without affecting the properties of liquid flow through the channel. A gas bubble can be forced into the channel by applying a gas pressure at the opening using an external pneumatic actuator. The gas pressure forces the meniscus inside the channel, which varies the flow of liquid through the channel interior.

According to one embodiment, the microchannel includes a hydrophobic patch spanning the width of the microchannel at the location where the gas bubble is introduced to enhanced on-off switching of the bubble valve. The hydrophobic patch anchors the bubble in a particular location in the microchannel. If the introduced gas bubble covers the whole area of the patch, the bubble is effectively retained by capillary forces and blocks any liquid flow up to a certain pressure difference, depending on the level of hydrophobicity of the patch.

Alternatively or in combination with a hydrophobic patch, the microchannel can be locally shaped into a cavity for receiving and anchoring the gas bubble. By providing an appropriate cavity, the bubble can be kept in place during operation, reducing the risk that the gas bubble is carried away with the liquid.

According to one aspect of the invention, a microfluidic device is provided. The microfluidic device comprises a microchannel having an interior bounded by a side wall and a valve for regulating the flow of fluid through the microchannel. The valve comprises a gas-filled reservoir, a fluid meniscus interfacing the reservoir and the interior and an actuator for varying the volume of the reservoir to increase an internal pressure of the reservoir to vary the flow of liquid through the channel.

According to another aspect, a microfluidic device is provided, comprising a first plate having a groove formed therein defining a microchannel, a second plate for enclosing the microchannel and a flexible membrane. The second plate is bonded to the first plate and has an aperture adjacent to the groove sized and dimensioned to form a meniscus when the microchannel is filled with a liquid. The aperture defines a reservoir adjacent to the microchannel, wherein the meniscus forms an interface between the microchannel and the reservoir. The flexible membrane is bonded to the second plate to seal the reservoir.

According to another aspect, a method of making a bubble valve is provided, the method comprises providing a microchannel having an interior bounded by a side wall, an aperture formed in the side wall and a valve chamber adjacent to the aperture in communication with the interior, filling the microchannel with a liquid to form a meniscus of the liquid in the aperture, whereby the step of filling traps a gas in the valve chamber and providing an actuator for increasing the pressure in the valve chamber to deflect the meniscus into the interior.

According to yet another aspect, a method of making a bubble valve is provided. The method comprises providing a microchannel having an interior bounded by a side wall, an aperture formed in the side wall and a valve chamber adjacent to the aperture in communication with the interior, filling the microchannel with a liquid to form a meniscus of the liquid in the aperture and applying and sealing an actuator comprising a chamber to a top surface of the microchannel to form a gas-filled chamber adjacent to the meniscus. The actuator varies the pressure in the gas-filled chamber to deflect the meniscus into the interior, thereby regulating fluid flow.

According to still another aspect, a microfluidic device is provided comprising a microchannel having an interior bounded by a side wall, a bubble valve for creating and injecting a bubble into the microchannel interior to regulate fluid flow through the microchannel and a hydrophobic patch for retaining the bubble in a predetermined position in the microchannel interior.

According to yet another aspect a bubble valve in a particle sorting device for separating particles having a predetermined characteristic from particles not having a predetermined characteristic is provided. The bubble valve comprises a gas-filled reservoir, a side channel in communication with a channel through which a stream of particles in a carrier fluid passes, wherein the carrier fluid forms a meniscus in the side channel adjacent to the gas-filled reservoir and an actuator for deflecting the meniscus to create a pressure pulse to selectively deflect a particle having the predetermined characteristic from the stream of particles.

According to still another aspect, a method of varying an electrical resistance in a microchannel is provided. The method comprises generating a bubble and injecting the bubble into a liquid in the microchannel, whereby the bubble varies the electrical resistance of the microchannel.

According to yet another aspect, an electrophoretic system is provided, comprising an electrokinetically operated microchannel, a sample well for providing an sample to the microchannel, a voltage source and a bubble valve for injecting a bubble into the microchannel to vary the electrical resistance of the microchannel.

According to a final aspect of the invention, an electrokinetic column to column switch is provided, comprising a first electrokinetically operated microchannel, a second electrokinetically operated microchannel in communication with the first electrokinetically operated microchannel and a bubble valve for selectively blocking flow from the first electrokinetically operated microchannel to the second electrokinetically operated microchannel by selectively injecting a bubble into a microchannel.

DETAILED DESCRIPTION OF THE INVENTION

The present invention provides an improved bubble valve for controlling fluid flow through a microchannel in a microfluidic system. The invention further provides a method of forming the bubble valve. The bubble valve of the present invention can be applied in numerous microfluidic systems for controlling and switching fluid flows. Examples of suitable applications include, but are not limited to: flow cytometry, column switching, 2-D separations, cell or particle sorting applications on a chip, regulating pressurized fluid flows including on-off switching, regulating electrokinetic fluid flows and electrokinetically induced processes including on-off switching and electrokinetic sample injection and channel to channel switching.

Figure 1:
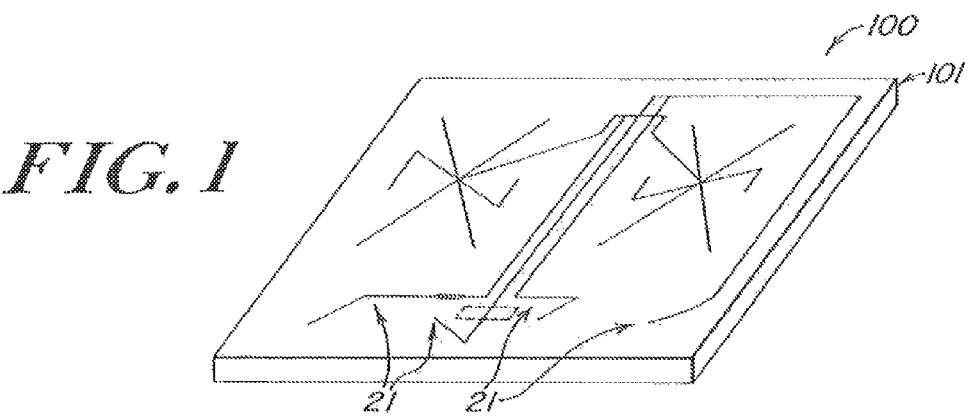
FIG. 1 is a schematic view of a microfluidic system suitable for implementing the illustrative embodiment of the invention.

FIG. 1 illustrates a microfluidic system suitable for implementing the illustrative embodiment of the present invention. The illustrative microfluidic system 100 comprises a substrate 101 having one or more microchannels 21 disposed therein. The microchannels transport fluid through the microfluidic system 100 for processing, handling, and/or performing any suitable operation on a liquid sample. As used herein, the term "microfluidic" refers to a system or device for handling, processing, ejecting and/or analyzing a fluid sample including at least one channel having microscale dimensions. The term "channel" as used herein refers to a pathway formed in or through a medium that allows for movement of fluids, such as liquids and gases. The term "microchannel" refers to a channel preferably formed in a microfluidic system or device having cross-sectional dimensions in the range between about 1.0 μm and about 500 μm, preferably between about 25 μm and about 250 μm and most preferably between about 50 μm and about 100 μm. One of ordinary skill in the art will be able to determine an appropriate volume and length of the microchannel. The ranges are intended to include the above-recited values as upper or lower limits. The microchannel can have any selected shape or arrangement, examples of which include a linear or non-linear configuration and a U-shaped configuration. The microfluidic system 100 may comprise any suitable number of microchannels 21 for transporting fluids through the microfluidic system 100.

The microfluidic system 100 includes a bubble valve 10, 10' shown in FIGS. 2-8c for controlling liquid flow through a microchannel of the system. According to the illustrative embodiment, the microchannel is defined by a side wall having any suitable shape enclosing at least a portion of the interior of the channel. The bubble valve may be formed by a gas-filled reservoir positioned adjacent to the microchannel including a meniscus that forms the interface between the reservoir and the microchannel interior. The meniscus may form a portion of the side wall of the microchannel. The bubble valve includes an actuator for modifying the pressure in the reservoir to deflect the meniscus into the channel interior, thereby modifying the cross-sectional area of the microchannel and consequently varying the flow of liquid through the channel.

According to an alternate embodiment, the bubble valve is formed by a meniscus in a separate side channel that communicates with and intersects a microchannel through which a liquid to be controlled flows. One skilled in the art will recognize that the meniscus can be located at any location relative to the microchannel through which liquid flows.

The gas-filled reservoir may be formed when filling the microchannel having an aperture in a side wall and a reservoir formed adjacent to the aperture. An empty microchannel may be filled with liquid, forming the meniscus in the aperture, which traps the gas that forms the gas bubble and forms a gas pocket in the reservoir adjacent to the meniscus. The creation of the gas pocket on filling provides a sterile gas bubble and reduces contaminants in the system. Alternatively, the air pocket may be created by introducing a gas to the reservoir after filling of the microchannel.

Figure 2:
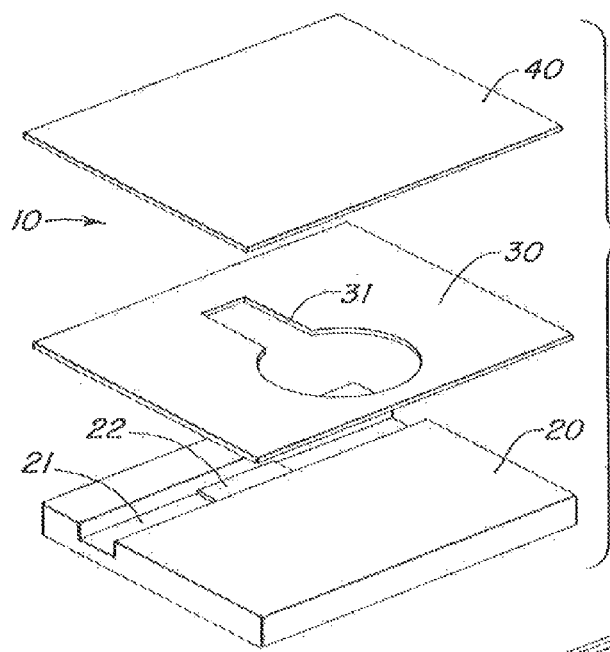
FIG. 2 shows an exploded view of a bubble valve according to an illustrative embodiment of the present invention.

FIG. 2 shows an exploded view of an embodiment of an illustrative bubble valve 10 of the present invention. The microfluidic system may be formed by a plurality of stacked layers. As shown in FIG. 2, the illustrative microfluidic system 100 includes a first plate 20 in which a groove defining the microchannel 21 is provided. A hydrophobic patch 22 may be applied to an inner wall of the microchannel 21. A second plate 30 for enclosing the microchannel is bonded to the first plate 20 and includes an aperture 31. A third plate 40 is bonded on top of second plate 30 to close and seal the stacked structure. The aperture 31 of the intermediate second plate 30 defines a void in the system adjacent to the microchannel 21.

Figure 3:
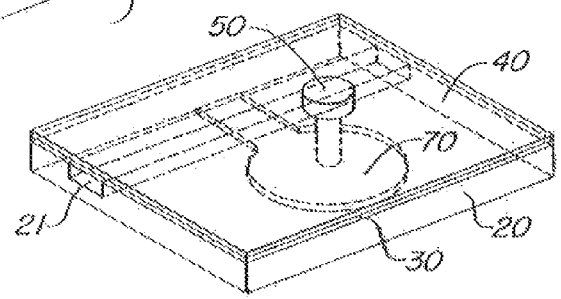
FIG. 3 shows an isometric view of the bubble valve of FIG. 2.
Figure 4:
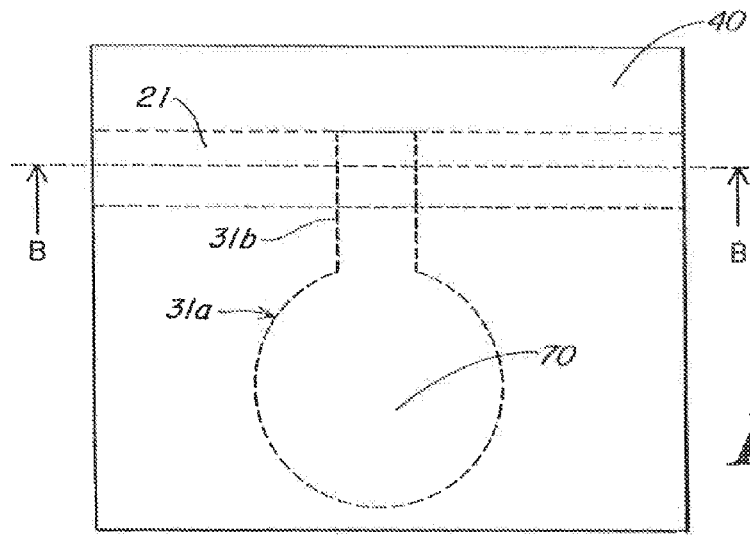
FIG. 4 shows a top view of the bubble valve of FIG. 2.

FIGS. 3 and 4 illustrates the assembled bubble valve 10. As shown, the stacked first plate 20, second plate 30 and third plate 40 define a closed, gas filled gas reservoir 70, which can be actuated with a displacement actuator 50. According to the illustrative embodiment, the aperture 31 defining the reservoir 70 comprises a main body 31a and a slot 31b extending from the main body 31a. When the microfluidic system 10 is assembled, the slot 31b of the aperture 31 defines a gap in the side wall of the microchannel 21 that provides access to and communicates with the interior of the microchannel 21.

The bubble valve 10 operates to control the flow of liquid through the microchannel 21. A meniscus is formed in the aperture 31, which interfaces with and separates the microchannel interior from the reservoir 70. According to the embodiment shown in FIGS. 2-8c, the meniscus is formed by a liquid filling the microchannel in the slot 31b. One skilled in the art will recognize that other suitable devices may be used to form the meniscus. The liquid in the slot 31b is retained in the microchannel by capillary forces. The actuator 50 deflects the upper wall of the reservoir, defined by plate 40, which decreases the volume of the reservoir 70. The actuator 50 may comprise any suitable device for deflecting the wall, such as an electromagnetic actuator or a piezoelectric element. The plate 40 may comprises a flexible membrane. The decreased volume consequently increases the pressure of the reservoir 70 and causes the meniscus 80 to deflect into the channel interior to create a constriction in the channel, thereby impeding fluid flow or pushing fluid away from the meniscus. If a sufficient pressure is applied to the meniscus, the actuator generates and enlarges a bubble in the liquid of the microchannel, which blocks fluid flow. The hydrophobic patch 22 provides an anchor for the bubble and retains the bubble at a selected location in the microchannel.

Figure 5A:
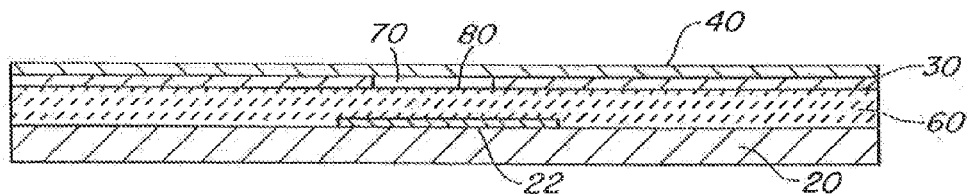
FIGS. 5a-c are cross-sectional views of the bubble valve of FIG. 2 in operation.
Figure 5B:
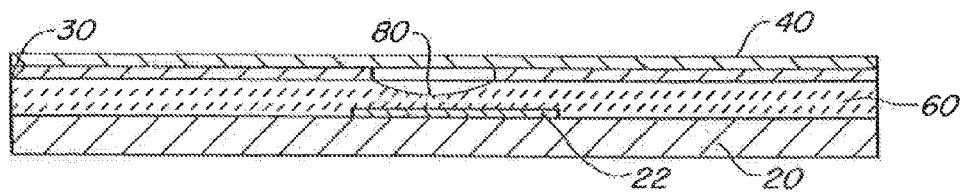
Figure 5C:
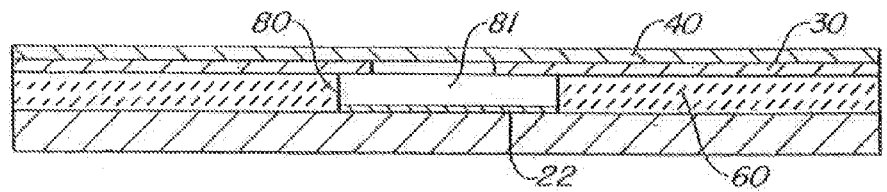

After the microchannel is filled with a liquid 60, the bubble valve 10 is ready for operation. FIG. 5a-c illustrate the operation of the bubble valve according to the teachings of the invention. FIG. 5a shows the bubble valve in an 'open' state. According to the embodiment of FIGS. 5a-5c, the meniscus between the reservoir and the interior of the microchannel is defined by the meniscus 80, formed by the liquid 60 in the slot 31b in the second plate 30. In the 'open' state, liquid flows freely through the microchannel 21 and the valve does not impose any additional flow resistance in the channel.

The slot 31b may be sized and dimensioned to form a "virtual wall" in the microchannel. As used herein, "virtual wall" refers to the meniscus 80 formed by the first liquid 60 in the aperture formed in the side wall of the microchannel 20, which essentially replaces the removed portion of the side wall without affecting the properties of the microchannel. The meniscus surface can be, although not required, substantially co-planar with the wall of the microchannel in which the meniscus is formed. The word "virtual" is chosen to express the effect that the overall liquid flow through the microchannel 21 of the microfluidic system 100 is not influenced by the virtual wall, i.e. the flow of liquid in the microfluidic system having a virtual wall is substantially identical to the flow of liquid through an identical microfluidic system in which no virtual wall is present. One of ordinary skill will recognize that the meniscus may be convex or concave, depending on the appropriate system pressure.

When the actuator 50 is actuated, the bubble valve 10 switches to a "pinched" state, as shown in FIG. 5b, to inhibit fluid flow through the channel interior. In the 'pinched' state, the actuator 50 deflects the top of the gas reservoir 70 for a certain fraction, increasing the pressure in the reservoir 70 and forcing the meniscus 80 down into the channel 21. The deflection of the meniscus locally reduces the cross-section of the channel 21 and introduces an additional flow resistance to the liquid flow. The degree of reduction in the liquid flow through the microchannel corresponds to the amplitude, frequency and duration of the displacement of the meniscus 80, which are controllable by the actuator 50. One skilled in the art will recognize that any suitable means for varying the pressure within the reservoir 70 may be used to deflect the meniscus 80, thereby regulating fluid flow.

When the actuator is fully actuated, the bubble valve 10 is switched to a closed state, as illustrated in FIG. 5c. As shown, in the closed state, the meniscus 80 deflects fully to form and introduce a gas bubble 81 into the microchannel 21. The gas bubble 81 is retained by the hydrophobic patch 22 formed in the channel wall opposite the slot 31b. As a result, the liquid flow in the channel is substantially blocked. By reducing the pressure on the meniscus 80, the bubble valve 10 can be brought from the 'closed' state of FIG. 5c via the 'pinched' state of FIG. 5b back to the 'open' state of FIG. 5a.

According to one embodiment, the bubble valve 10 may be used as a check valve for regulating pressure in the microchannel. When the pressure in the microchannel exceeds a maximum breaking pressure, the bubble collapses, opening the valve and allowing fluid to flow through the channel, thereby reducing the pressure in the microchannel. The breaking pressure depends on the hydrophobicity of the hydrophobic patch 22, as well as the geometry of the microchannel.

Alternatively or in combination with the hydrophobic patch 22, the microchannel 21 can be locally shaped into a cavity for receiving and anchoring the gas bubble 81. By providing an appropriate cavity, the bubble can be kept in place during operation, reducing the risk that the gas bubble is carried away with the liquid.

According to the embodiments shown in FIGS. 2-5c, the actuator 50 is integrated in the microfluidic chip 100. However, one skilled in the art will recognize that an external, reusable actuator may also be used to control formation of a gas bubble in the microchannel.

Figure 6:
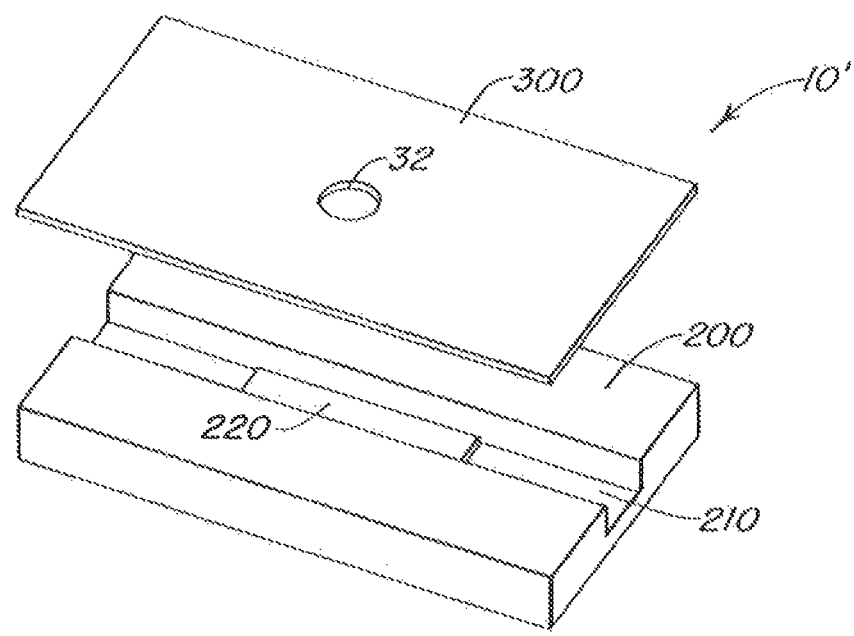
FIG. 6 shows an exploded view of an alternative embodiment of a bubble valve according to the present invention.

FIG. 6 shows an alternative embodiment of a microfluidic system 100' including a bubble valve 10' having an external actuator 90 according to the teachings of the invention. In the embodiment shown in FIG. 6, the microfluidic system 100' includes a first plate 200 including a groove defining the microchannel 210 and a second plate 300 bonded to the first plate 200 for enclosing the microchannel 210 and in which a virtual wall opening 32 is formed. The virtual wall opening 32 is sized and dimensioned to form a "virtual wall" when the microchannel 210 is filled with a liquid.

Upon filling of the microchannel 21 with a liquid, a virtual wall 32a is formed in virtual wall opening 32. As shown in FIGS. 7, 8a-8c, the microfluidic system further includes an external actuator, illustrated as pressurizer 90, pressed and sealed onto the top of the second plate 300 to form a tight seal. The external pressurizer 90 defines a sealed pressurizing chamber 92 adjacent to the virtual wall 32a. The pressurizer varies the pressure within the pressurizing chamber 92 to control liquid flow through the microchannel 210 by modifying the position of the virtual wall. The pressurizer 90 may include a source of pressurized gas (not shown) and a gas inlet 91 to allow a gas pressure to be applied to the virtual wall 32a in order to move the virtual wall. The pressurizer may alternatively include a flexible wall that deflects to vary the volume of the chamber 92 upon activation of an actuator, such as a piezoelectric element or electromagnetic actuator.

Figure 7:
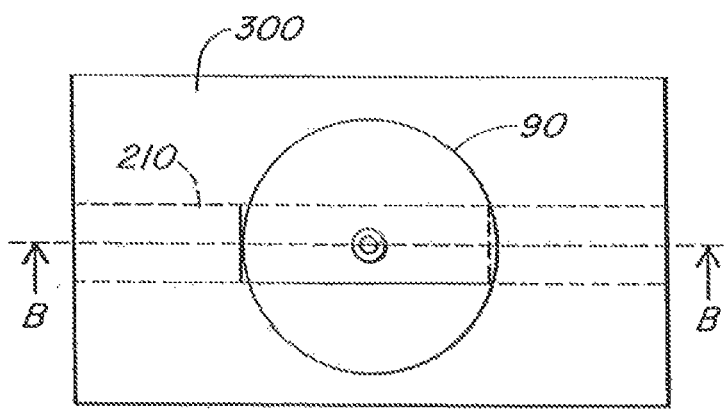
FIG. 7 shows a top view of the bubble valve of FIG. 6.
Figure 8A:
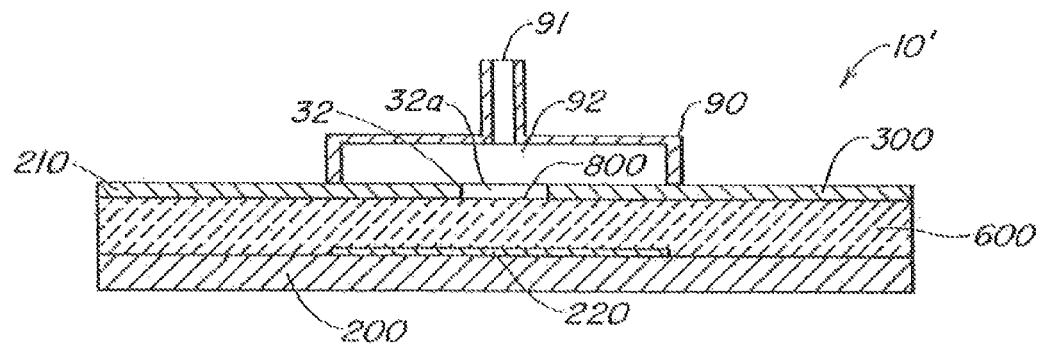
FIGS. 8a-c are cross-sectional view of the bubble valve of FIG. 6 in operation.

FIG. 8a shows a cross-section of the bubble valve 10' of FIGS. 6 and 7 in the 'open' state. As shown, when the microchannel 210 is filled with liquid 600, a virtual wall 32a, defined by a meniscus 800, is formed within the virtual wall opening 32. The meniscus essentially replaces the absent portion of the side wall of the microchannel and allows liquid to flow through the channel interior unimpeded and uninfluenced by the virtual wall.

Figure 8B:
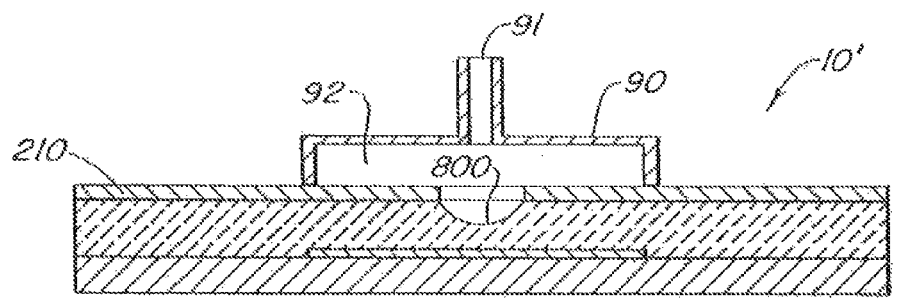

FIG. 8b depicts the 'pinched' state of the bubble valve, when the pressurizer 90 is activated. As shown, activation of the pressurizer 90 increases the internal pressure within the pressurizing chamber 92. The increased pressure moves the meniscus 800 down the channel height and into the microchannel interior, thereby regulating liquid flow. The pressurized controls the level of the internal pressure in order to control the amount of deflection of the meniscus and therefore the rate of fluid flow.

Figure 8C:
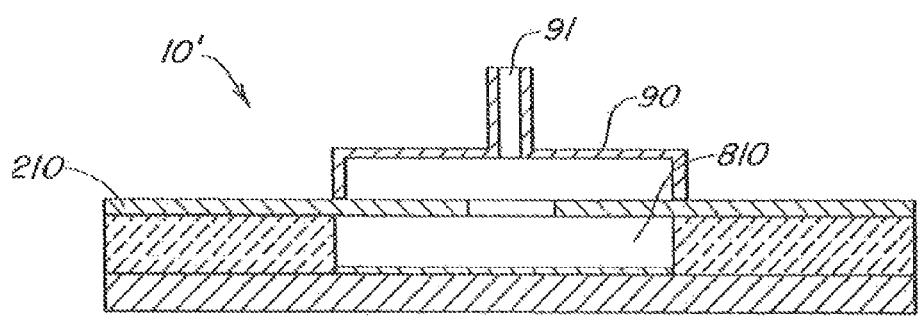

To switch the valve to a 'closed' state, as shown in FIG. 8c, the pressurizer 90 applies a large pressure that is sufficient to form and introduce a gas bubble 810 into the channel 210. The hydrophobic patch 220 retains the gas bubble 810 in place. As a result, the liquid flow in the channel is blocked up to a 'breaking pressure', which depends on the hydrophobicity of hydrophobic patch 220. A higher hydrophobicity results in a larger breaking pressure. By reducing the pressure on the meniscus 800 the bubble valve 10' can be brought from the 'closed' state of FIG. 8c via the 'pinched' state of FIG. 8b back to the 'open' state of FIG. 8a.

Figure 9:
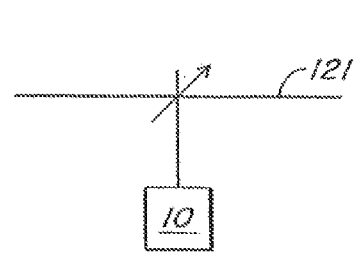
FIG. 9 shows an application of the bubble valve of an illustrative embodiment of the present invention in a microchannel.

FIG. 9 shows an application of a bubble valve 10 for flow regulation in a microchannel 121 according to one embodiment of the invention. During typical operation of a microfluidic system, a pressure difference is applied over the length of a microchannel 121. A bubble valve 10 can be employed to regulate the flow through the microchannel between zero and a maximum flow rate, depending on the applied pressure difference.

Figure 10:
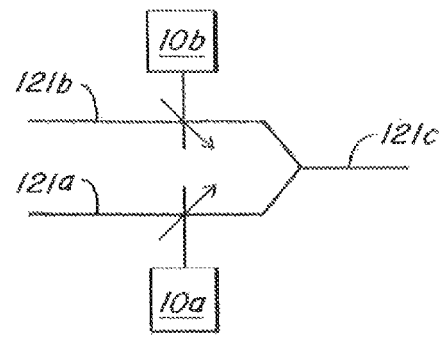
FIG. 10 shows a Y-intersection in a microfluidic system of an embodiment of the invention that implements a bubble valve to control liquid flow according to the teachings of the present invention.

FIG. 10 shows a portion of a microfluidic system according to an embodiment of the invention forming a Y-intersection comprising two inlet microchannels 121a and 121b and an outlet channel 121c that combines the fluids flowing through the two inlet microchannels. The first microchannel 121a carries a first liquid and the second microchannel 121b carries a second liquid. The microchannels 121a and 121b are each controlled by a corresponding bubble valve, 10a and 10b, respectively, for regulating the combined composition and flow rate through the outlet microchannel 121c. One skilled in the art will recognize that that the number of inlet channels is not limited to two, but is presented here merely as an example.

Figure 11:
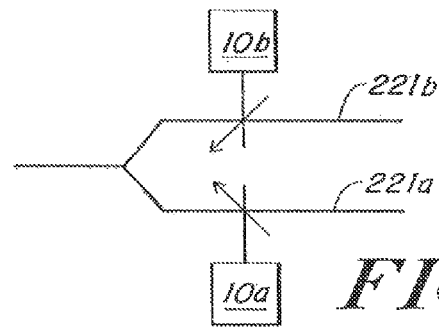
FIG. 11 shows a Y-intersection in a microfluidic system of another embodiment of the invention that implements a bubble valve to control liquid flow according to the teachings of the present invention.

FIG. 11 shows a Y-intersection of a microfluidic system according to another embodiment of the invention. As shown the Y-intersection comprises an inlet microchannel 221c and two outlet microchannels 221a and 221b for splitting the incoming liquid flow from the inlet microchannel 221c. The flow of each outlet channel is regulated by a corresponding bubble valve 200a and 200b, respectively. The incoming liquid flow from the inlet microchannel 221c can be split between microchannel 221a and microchannel 221b in any required ratio. One skilled in the art will recognize that that the number of inlet channels is not limited to two, but is presented here merely as an example.

Figure 12B:
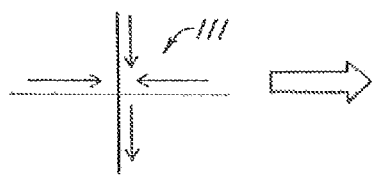
FIGS. 12a-c shows an electrophoresis system that implements a bubble valve to control electrical current during electrokinetic injection according to the teachings of the present invention.
Figure 12C:
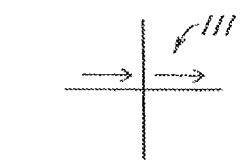
Figure 12A:
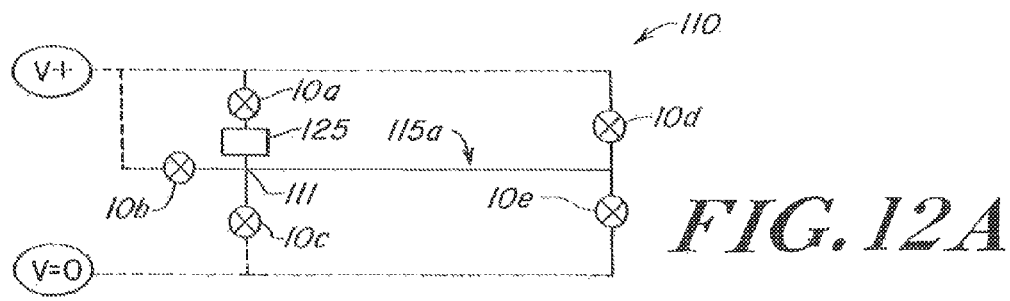

FIG. 12a-12c shows the implementation of an electrophoresis system 110 comprising five bubble valves, 10a-e of the present invention, arranged with a crossed microchannel configuration. Regulation of the bubble valve 10a regulates the electric current through the associated electrokinetically operated microchannel 115a. The pinching of the liquid in the electrokinetically operated microchannel 115a by a bubble valve will result in an increased electrical resistance in the microchannel 115a. As a result, the migration of charged species and electro-osmotic flow in the electrokinetically operated microchannel 115a can be regulated. A voltages difference for the injection of sample from a well storing a supply of a sample 125 between the bubble valve 10a and the crossing point 111 of the microchannels and consecutive separation are provided via wells V+ and V0. Electrodes are placed in the V+ and V0 wells and energized with a constant voltage difference during the operation of the electrophoresis system.

In the injection phase, valves 10a, 10b, 10c and 10d are substantially in the open position, allowing passage of electrical current up to a required level for injection (FIG. 12b shows direction of current/sample), while bubble valve 10e is closed. The valves are kept in this position long enough for the sample to move from the sample well 125 towards and past the central injection crossing 111. Varying the opening ratio of valves 10a, 10b and 10d can be adjusted to confine the sample to a narrow flow through the injection cross 111, as shown in FIG. 12c (i.e. 'pinched injection').

Immediately after the injection phase, a plug of sample is injected and separated in the separation column 115a (microchannel which runs horizontally in figure) by closing bubble valves 10a, 10d and 10c and opening valves 10b and 10e. Now the total voltage difference is applied longitudinally over the separation channel, resulting in the separation of the constituents in the sample (FIG. 12c).

Figure 13A:
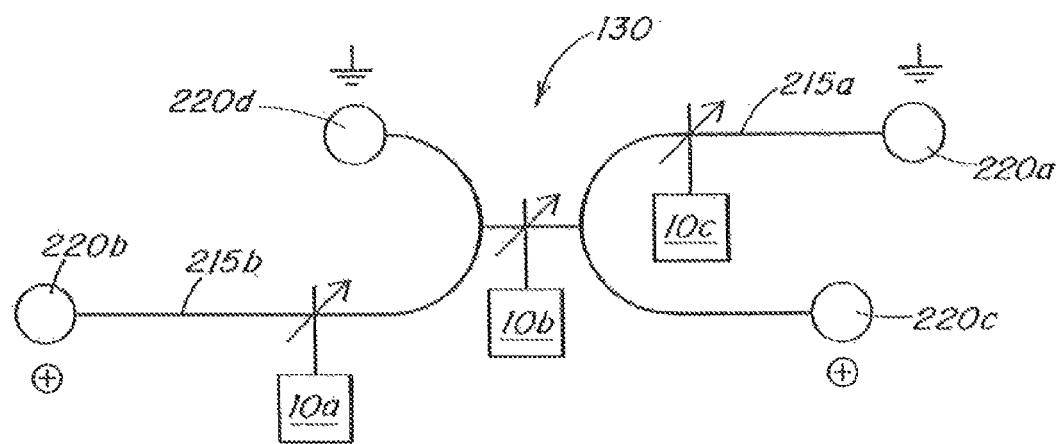
FIG. 13a shows an electrokinetic column-column switch implementing a bubble valve according to the teachings of the present invention.

FIG. 13a illustrates another application of the bubble valve of the present invention implemented in a column-column switch 130 for electrokinetically transferring a substance from a first electrokinetically operated microchannel 215a to a second electrokinetically operated microchannel 215b. The column-column switch 130 comprises a bubble valve 10b of the present invention that connects the first electrokinetically operated microchannel 215a to the second electrokinetically operated microchannel 215b. Both electrokinetically operated microchannel 215a and electrokinetically operated microchannel 215b are connected to corresponding wells well 220a-d. In the following example, it is assumed that the substances electrokinetically move from a positive electric potential to ground and that well 120c and well 120b are provided with a positive potential whilst well 120a and well 120d are grounded.

At first, the two electrokinetically operated microchannel 215a and electrokinetically operated microchannel 215b are operated independently and the connecting bubble valve 10b is in the 'closed' state whilst bubble valve 10a and bubble valve 10c are in the 'open' state. To electrokinetically transfer substance from electrokinetically operated microchannel 215a to the electrokinetically operated microchannel 215b, bubble valve 10a and bubble valve 10c are switched to the closed state, and the connecting bubble valve 10b is opened momentarily to allow passage of an amount of substance from the electrokinetically operated microchannel 215a to the electrokinetically operated microchannel 215b. The amount transferred depends directly upon the time bubble valve 10b is opened. After the required amount of substance is transferred, the connecting bubble valve 10b is closed and the bubble valve 10a and bubble valve 10b are opened again.

Figure 13B:
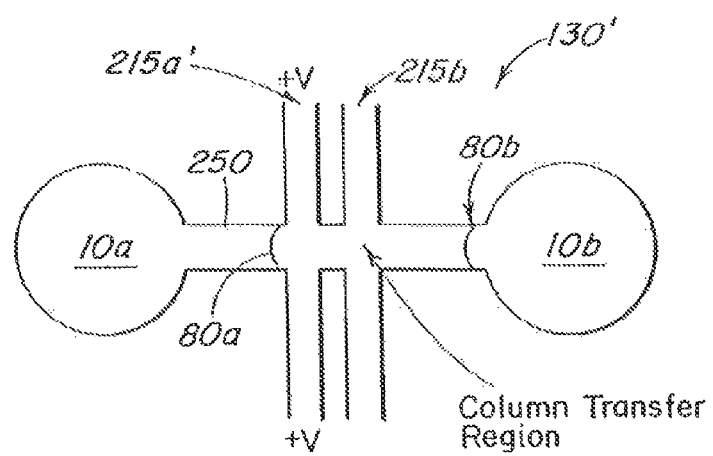
FIG. 13b shows an alternate electrokinetic column-column switch implementing a bubble valve according to another embodiment of the present invention.

FIG. 13b illustrates the implementation of another column to column switch 130' to exchange liquid from a first column 215a' selectively into a second column 215b'. The first column and the second column are each crossed by a transfer column 250, operated by a first bubble valve 10a arranged on one end of the transfer column 250 and a second bubble valve 10b arranged on the opposite end of the transfer column 250. The first one of the bubble valves is attached to the first column 215a' and is actuated upon transiently by an external actuator for increasing the pressure within the bubble valve reservoir. Increasing the pressure on the bubble valve will deflect the meniscus 80, inducing a transient flow in the transfer column 250 from the pressurized bubble valve 10a towards the second bubble valve 10b, which comprises a compressible volume of gas. This transient flow effectively transfers a liquid volume from the first column 215a' to the second column 215b'. Upon deactivation of the external actuator, the flow in the transfer column 250 reverses as the compressed gas volume in the second bubble valve 10b exerts a pressure on the liquid in the transfer column 250.

Figure 14:
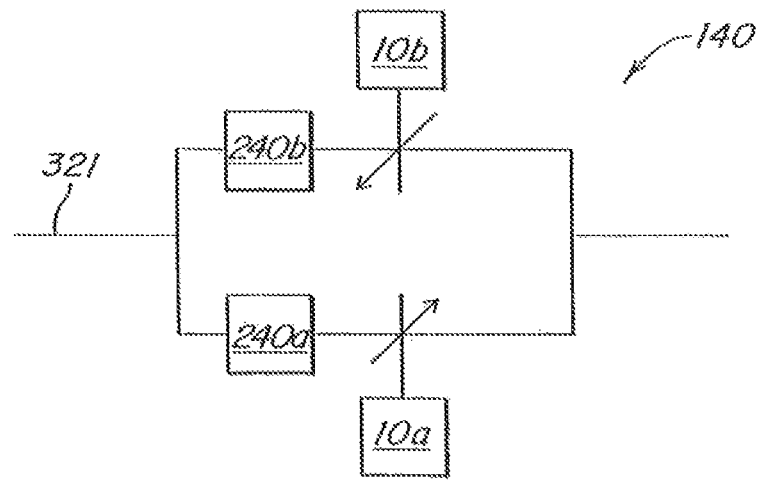
FIG. 14 shows a selective resistance circuit that employs a bubble valve to control electrical current according to the teachings of the present invention.

FIG. 14 shows a selective resistance circuit employing a bubble valve of the present invention for selectively including a predefined electrical resistance in an electrokinetic circuit. The circuit 140 comprises an inlet microchannel 321, which splits into two paths. The first path 322 includes a fluidic resistor 240a and a bubble valve 10a, the second parallel path 323 includes a fluidic resistor 240b and a bubble valve 10b. The fluidic resistors 240a-b comprise a channel of appropriate length to results in a certain electrical resistance. The bubble valve 10a and the bubble valve 10b can be switched each to either on to allow fluid flow through the associated microchannel or off to block fluid flow through the associated microchannel. As a result, the overall electrical resistance of the electrokinetic circuit can be switched between four values: infinite (both bubble valves 10a-b are off), the resistance of fluidic resistor 240a (bubble valve 10a on, bubble valve 10b off), the resistance of fluidic resistor 240b (bubble valve 10a off, bubble valve 10b on) and the parallel resistance of fluidic resistor 24a-b (both bubble valves 10a and 10b on).

Figure 15:
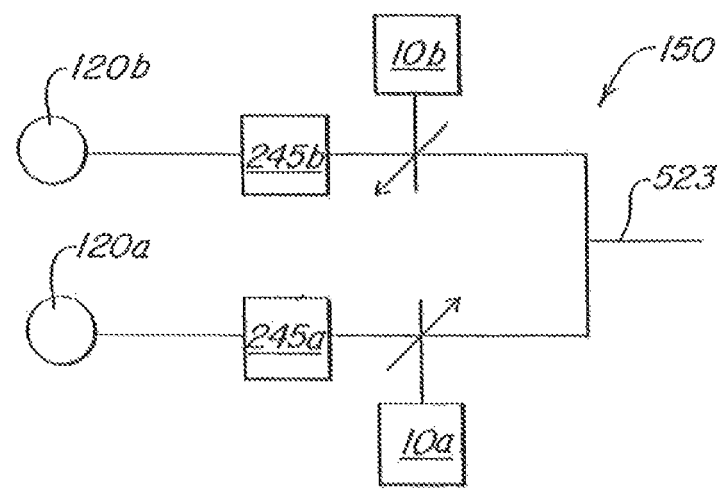
FIG. 15 shows an alternative selective resistance circuit that employs a bubble valve to control electrical current according to the teachings of the present invention.

FIG. 15 shows an alternative resistance circuit 150 according to another application of the invention, now for the selective application of a voltage. By opening either the bubble valve 10a or bubble valve 10b, the voltage imposed on an outgoing channel 523 can be selected. Fluidic resistor 245a and 245b function to limit the electric current in either of the two states to a predetermined value.

Figure 16:
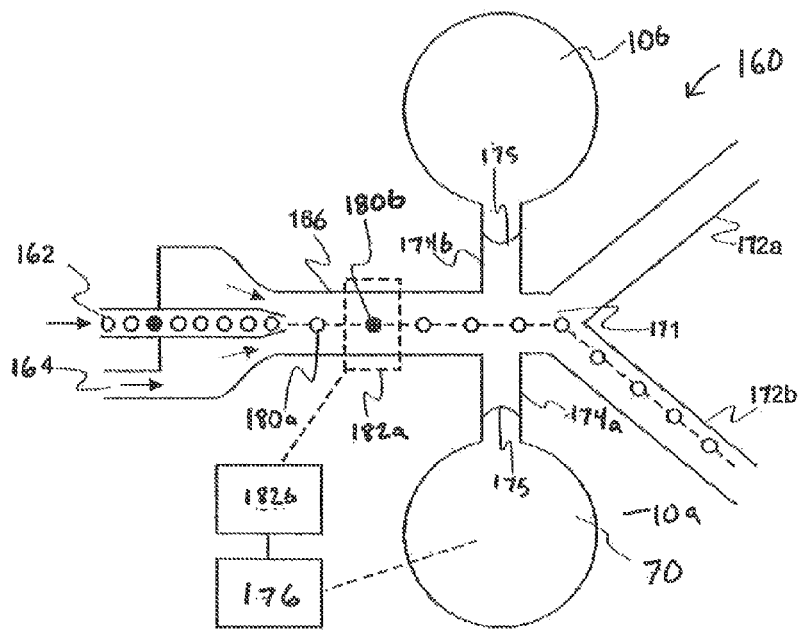
FIG. 16 shows a particle sorting system that implements a bubble valve of the present invention to produce fluid impulses to sort particles.

FIG. 16 illustrates another application of the bubble valve 10 of the present invention in a particle sorting application, wherein the bubble valve is positioned in a side channel that communicates with a channel through which particles in suspension flow. According to one application of the present invention, a particle sorter 160 comprises a closed channel system of capillary size for sorting particles, such as cells. The channel system comprises a first supply duct 162 for introducing a stream of particles and a second supply duct 164 for supplying a carrier liquid. The first supply duct 162 ends in a nozzle, and a stream of particles is introduced into the flow of carrier liquid. The first supply duct 162 and the second supply duct 164 enter a measurement duct 166, which branches into a first branch 172a and a second branch 172b at a branch point 171. A measurement region 182a is defined in the measurement duct 166 and is associated with a detector 182b to sense a predetermined characteristic of particles in the measurement region 182a. Two opposed bubble valves 10a and 10b are positioned in communication with the measurement duct 166 and are spaced opposite each other. The bubble valves 10a, 10b communicate with the measurement duct 166 through a pair of opposed side passages 174a and 174b, respectively. Liquid is allowed to partly fill these side passages 174a and 174b to form a meniscus 175 therein. An external actuator 176 is also provided for actuating the bubble valves 10a, 10b, which momentarily causes a flow disturbance in the duct to deflect the flow therein when activated by the actuator 176.

In a suspension introduced by the first supply duct 162, two types of particles can be distinguished, normal particles 180a and particles of interest 180b. The flow rates in both branches 172a and 172b are adjusted so that the stream of particles normally flows through the second branch 172b. Upon sensing the predetermined characteristic in the particles in the measurement region 182a, the detector 182b raises a signal. The external actuator 176 activates the bubble valves 10a, 10b when signaled by the detector 182b in response to sensing the predetermined characteristic, to create a flow disturbance in the measurement duct 166 between the sideway passages 174a, 174b, to deflect the particle having the predetermined characteristic so that it flows down the first branch duct 172a rather than the second branch duct 172b. The detector communicates with the actuator 176, so that when the detector 182b senses a predetermined characteristic in a particle, the actuator activates the first bubble valve 10a to cause pressure variations in the reservoir 70 of the first bubble valve. The activation of the first bubble valves causes a transient pressure variation in the first side passage 174a. The second side passage 174b and the second bubble valve 10b absorb the transient pressure variations in the measurement duct 166 induced via the actuator 176. Basically, the reservoir 70b of the second bubble valve 10b is a chamber having a resilient wall or contains a compressible fluid such as a gas. The resilient properties allow the flow of liquid from the measurement duct into the second side passage 174b.

Figures 17A, 17B, 17C:
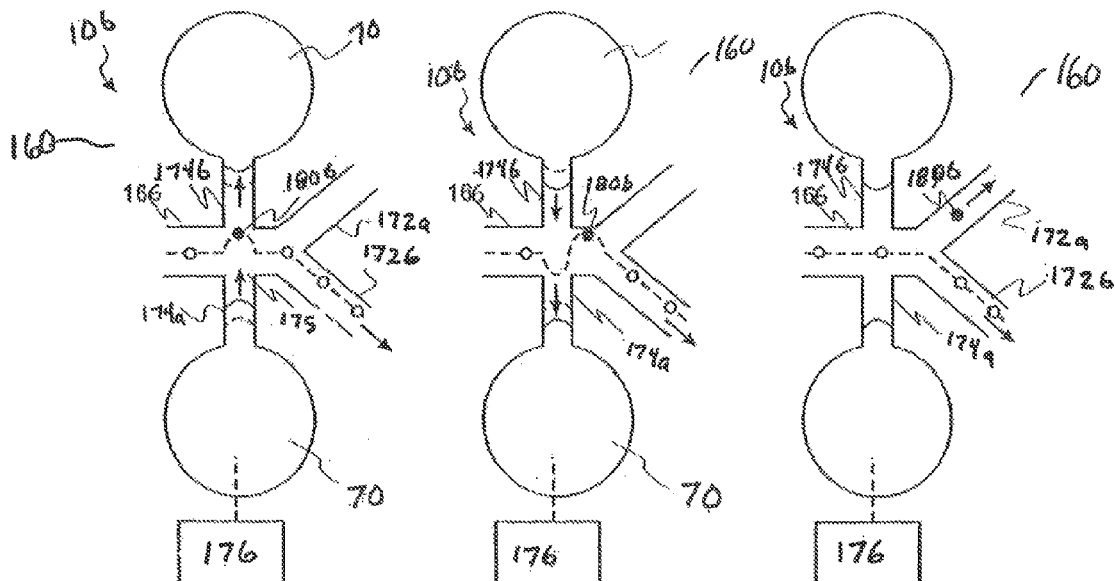
FIGS. 17a, 17b and 17c illustrate the operation of the particle sorting system of FIG. 16.

FIGS. 17a-17c illustrate the operation of the particle sorting system 160 of FIG. 16. In FIG. 17a, the detector raises a signal to activate the actuator. Upon activation of the actuator, the pressure within the reservoir of the first bubble valve 10a is increased, causing a transient discharge of liquid from the first side passage 174a as indicated by the arrow. The sudden pressure increase caused at this point in the duct causes liquid to flow into the second side passage 174b because of the resilient properties of the reservoir of the second bubble valve 10b. This movement of liquid into the second side passage 174b is indicated with an arrow. Resultingly, as can be seen in the figure, the flow through the duct is deflected causing the selected particle of interest 178b located between the first side passage 174a and the second side passage 174b to be shifted perpendicular to its flow direction in the normal state. The flow resistances to the measurement duct 166, the first branch 172a and the second branch 172b is chosen so that the preferred direction of the flow to and from the first side passage 174a and the second side passage 174b has an appreciable component perpendicular to the normal flow through the measurement duct 166. This goal can for instance be reached by the first branch 172a and the second branch 172b so that their resistances to flow is large in comparison with the flow resistances of the first side passage 174a and the second side passage 174b.

FIG. 17b shows the particle sorting system 160 during the relief of the first bubble valve reservoir when the particle of interest 178b has left the volume between the first side passage 174a and the second side passage 174b. The actuator 176 is deactivated, causing the pressure inside the reservoir to return to the normal pressure. During this relief phase there is a negative pressure difference between the two reservoirs of the bubble valves, causing a liquid flow through the first side passage 174a and the second side passage 174b opposite to the liquid flow shown in the previous figure and is indicated by the arrows.

FIG. 17c shows the particle sorting system 160 after completion of the switching sequence. The pressures inside the reservoirs of the bubble valves has been equalized so the flow through the measurement duct 166 is normalized. As the particle of interest 178b has been displaced radially, it will flow into the first branch 172a as was the objective of the switching operation.

According to yet another embodiment, the cross-sectional dimensions of a microchannel including a bubble valve according to the teachings of the present invention may be varied locally to affect the pressure within the microchannel interior. For example, the microchannel may be narrowed or widened at certain locations to increase or decrease the capillary forces acting on a fluid in the microchannel interior. One of ordinary skill in the art will be able to determine a suitable cross-sectional dimension to achieve a desired pressure within the microchannel interior.

The bubble valve of the present invention may be implemented in a variety of microfluidic devices used for many applications. In a particular application, the bubble valve is implemented in a flow-cytometer based instrument for sorting or physically separating particles of interest from a sample or for measuring selected physical and chemical characteristics of cells or particles in suspension as they travel past a particular site. The bubble valve may also be employed in devices for sequencing or manipulating DNA, medical diagnostic instruments, devices for drug discovery, chemical analysis and so on.

The present invention provides an improved system and method for regulating fluid flow in a microchannel for a variety of applications. The bubble valve of the present invention is easy to operate and control, simple to manufacture and economical. In addition, the bubble valve does not adversely affect the liquid in the microchannel. The bubble valve effectively controls the flow of liquids in microfluidic systems, without heating the fluid and without complex on-chip circuitry.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

What is claimed is:

1. A method for facilitating analysis or processing of a sample, the method comprising:
   flowing a sample through a microfluidic flow channel formed in a substrate;
   propagating a pressure pulse across the microfluidic flow channel in a crosswise direction; and
   dampening or absorbing the pressure pulse using a first reservoir in fluid communication with the microfluidic flow channel,
   wherein the pressure pulse is used to sort one or more particles suspended within the sample.

2. The method of claim 1, wherein the pressure pulse is used to selectively control or otherwise affect the flow of the sample through the flow channel.

3. The method of claim 1, wherein the first reservoir includes a gas pocket, wherein compression of the gas facilitates the dampening or absorbing of the pressure pulse.

4. The method of claim 1, wherein the first reservoir includes a resilient wall for facilitating dampening or absorbing of the pressure pulse.

5. A microfluidic device adapted to facilitate analysis or processing of a sample, the microfluidic device comprising:
   a microfluidic flow channel formed in a substrate, the flow channel having a width and a length that exceeds the width; and
   a first reservoir in fluid communication with the flow channel adapted for dampening or absorbing a pressure pulse propagated across the width of the flow channel, wherein the first reservoir is otherwise sealed from an exterior environment.

6. The device of claim 5, wherein the first reservoir includes resilient properties which enable the dampening or absorbing the pressure.

7. The device of claim 6, wherein the resilient properties of the first reservoir include a gas pocket, wherein compression of the gas facilitates the dampening or absorbing of the pressure pulse.

8. The device of claim 7, further comprising a fluid filled region interfacing with the flow channel and the gas pocket.

9. The device of claim 8, wherein the fluid filled region includes a portion of the first reservoir.

10. The device of claim 8, wherein the fluid filled region includes a side channel connecting the first reservoir to the flow channel.

11. The device of claim 8, wherein the fluid filled region prevents the gas from the gas pocket from leaking into the flow channel.

12. The device of claim 6, wherein the resilient properties of the first reservoir include a resilient wall for facilitating dampening or absorbing of the pressure pulse.

13. The device of claim 5, further comprising an actuator or pressurizer operatively associated with flow channel and adapted for generating the pressure pulse across the width of the flow channel.

14. The device of claim 5, further comprising a second reservoir operatively associated with the flow channel and adapted for generating the pressure pulse based on a change in volume or pressure in the second reservoir.

15. The device of claim 14, wherein the second reservoir includes a gas pocket, wherein compression of the gas facilitates the generating of the pressure pulse.

16. The device of claim 5, wherein the flow channel includes a branched portion, wherein the pressure pulse is used to sort one or more particles suspended within the sample into a selected branch of the branched portion.

17. The device of claim 5, wherein the first reservoir is adjacent to an aperture in a sidewall of the flow channel.

18. A method comprising:
   providing the microfluidic device of claim 5;
   flowing a sample through the microfluidic flow channel;
   propagating the pressure pulse across the width of the flow channel; and
   dampening or absorbing the pressure pulse using the first reservoir in fluid communication with the flow channel.

19. The method of claim 18, wherein the pressure pulse is used to sort one or more particles suspended within the sample.

* * * * *